(12) United States Patent
Barrett et al.

(10) Patent No.: US 6,440,434 B1
(45) Date of Patent: Aug. 27, 2002

(54) SKIN CARE COMPOSITION

(75) Inventors: Karen Elizabeth Barrett; Martin Richard Green, both of Bedford; Anthony Vincent Rawlings, Bebington, all of (GB)

(73) Assignee: Conopco, Inc., New York, NY (US)

( * ) Notice: Subject to any disclaimer, the term of this patent is extended or adjusted under 35 U.S.C. 154(b) by 0 days.

(21) Appl. No.: 09/627,968

(22) Filed: Jul. 28, 2000

(30) Foreign Application Priority Data

Jul. 30, 1999 (GB) ............................................. 9918022

(51) Int. Cl.[7] ........................ A61K 6/00; A61K 34/385; A61L 15/16; A01N 37/00
(52) U.S. Cl. ................... 424/401; 424/195.1; 424/448; 514/557
(58) Field of Search ............................ 424/401, 195.1, 424/448; 514/557

(56) References Cited

U.S. PATENT DOCUMENTS

| 5,536,740 A | * | 7/1996 | Granger et al. | 514/392 |
| 5,578,641 A | * | 11/1996 | Jackson et al | 514/547 |
| 5,599,548 A | * | 2/1997 | Granger et al. | 424/401 |
| 5,716,627 A | * | 2/1998 | Granger et al. | 424/401 |
| 5,747,051 A | * | 5/1998 | Granger et al. | 424/401 |
| 5,756,109 A | * | 5/1998 | Burger et al. | 424/401 |
| 5,759,556 A | * | 6/1998 | Burger et al. | 424/401 |
| 5,811,110 A | * | 9/1998 | Granger et al. | 424/401 |
| 5,935,596 A | * | 8/1999 | Crotty et al. | 424/448 |
| 5,955,092 A | * | 9/1999 | Granger et al. | 424/401 |
| 5,965,137 A | * | 10/1999 | Petrus | 424/195.1 |
| 6,022,896 A | * | 2/2000 | Weinkauf et al. | 514/557 |
| 6,042,841 A | * | 3/2000 | Alaluf et al. | 424/401 |
| 6,063,387 A | * | 5/2000 | Dorogi et al. | 424/401 |
| 6,071,541 A | * | 6/2000 | Murad | 424/616 |

FOREIGN PATENT DOCUMENTS

| EP | 116 439 | 8/1984 |
| EP | 709 084 | 5/1996 |
| EP | 711 558 | 5/1996 |
| EP | 0 888 773 A1 | * 1/1999 |
| WO | 93/19743 | 10/1993 |
| WO | 99/18913 | 4/1999 |

OTHER PUBLICATIONS

PCT International Search Report in a PCT application PCT/EP 00/06594., Jan. 2001.
Great Britain Search Report in a GB application GB 9918022.6., 1999.
Vahlquist, A. et al., J. Invest. Dermatol., Isotretinoin Treatment of Severe Acne Affects the Endogenous Concentration fo Vitamin A in Sebaceous Glands, vol. 94 Holland D.b. and Cunliffe, W.J. (1990) pp. 496–498.
Ellis, C.N. et al., Pharmacology of Retinoids in Skin, Treatment of Actinically Aged Skin with Topical Tretinoin, Vassel, Karger, vol. 3 (1989) pp. 249–252.
Lowe, N.J. et al., Pharmacology of Retinoids In Skin, Systemic Retinoids in Psoriasis: Comparative Efficacy and Toxicity, vol. 3 (1989) pp. 240–248.

\* cited by examiner

*Primary Examiner*—Michael G. Hartley
*Assistant Examiner*—Michael A. Willis
(74) *Attorney, Agent, or Firm*—Ellen Plotkin

(57) ABSTRACT

A topical application is provided which includes a petroselinic acid compound, a retinoid or an LRAT/ARAT inhibitor, and a dermatologically acceptable vehicle. These compositions are useful for treating or preventing normal, but undesirable, skin conditions selected from the group consisting of wrinkling, sagging, photodamage skin, dry skin and age spots and soothing sensitive skin.

15 Claims, No Drawings

SKIN CARE COMPOSITION

FIELD OF THE INVENTION

This invention relates to topical compositions for application to human skin and to their use in improving the condition and appearance of skin.

BACKGROUND OF THE INVENTION

Skin is subject to deterioration through dermatological disorders, environmental abuse (wind, air conditioning, and central heating) or through the normal aging process (chronoageing) which may be accelerated by exposure of skin to sun (photoageing). In recent years the demand for cosmetic compositions and cosmetic methods for improving the appearance and condition of skin has grown enormously.

Consumers are increasingly seeking "anti-ageing" cosmetic products that treat or delay the visible signs of chronoageing and photoageing skin such as wrinkles, lines, sagging, hyperpigmentation and age spots.

Consumers also frequently seek other benefits from cosmetic products in addition to anti-ageing. The concept of "sensitive skin" has also raised the consumer demand for cosmetic products that improve the appearance and condition of sensitive, dry and/or flaky skin and to soothe red, and/or irritated skin. Consumers also desire cosmetic products that have an oil/sebum control effect. Many people are concerned with the degree of pigmentation of their skin. For example, people with age spots or freckles may wish such pigmented spots to be less pronounced. Others may wish to reduce the skin darkening caused by exposure to sunlight or to lighten their natural skin colour. To meet this need many attempts have been made to develop products that reduce the pigment production in the melanocytes. However, the substances thus far identified tend to have undesirable side effects, e.g. skin irritation.

Consequently such substances are not suitable for cosmetic use or they can only be applied at a concentration at which their skin lightening effect is less than desired. Using a combination of different skin lightening substances may be considered to reduce adverse side effects but there is a substantial risk that by using such a combination the skin lightening is reduced as well due to competition effects. Therefore there is a need for improvement in the effectiveness of cosmetic skin lightening products particularly, such that they do not irritate the skin.

The use of fatty acids, including petroselinic acid, in cosmetic formulations for treating the hair is known. EP-A-116439) describes hair tonics which include fatty acids (such as petroselinic acid) for alleviating dandruff and itch and for stimulating hair growth.

EP-A 709084 describes the use of coriander seed oil, which is rich in petroselinic acid triglycerides, in a cosmetic composition for moisturising dry skin conditions. Retinol (vitamin A) is an endogenous compound that occurs naturally in the human body and is essential for normal epithelial cell differentiation. Natural and synthetic vitamin A derivatives (retinoids) have been used extensively in the treatment of a variety of skin disorders and have been used as skin repair or renewal agents. Retinoic acid, for example, has been employed to treat a variety of skin conditions, e.g., acne, wrinkles, psoriasis, age spots and discoloration. See e.g., Vahlquist, A. et al., J. Invest. Dermatol., Vol. 94, Holland D. B. and Cunliffe, W. J. (1990), pp. 496–498; Ellis, C. N. et al., "Pharmacology of Retinols in Skin", Vasel, Karger, Vol. 3, (1989), pp. 249–252; Lowe, N. J. et al., "Pharmacology of Retinols in Skin", Vol. 3, (1989), pp. 240–248, PCT Patent Application No. WO 93/19743.

There continues to be a need, however, for alternative effective cosmetic compositions for topical application to skin for treating/delaying the visible signs of aging and photodamaged skin such as wrinkles, lines, sagging, hyperpigmentation and age spots.

We have now found that effective treatment and prevention of normal, (but cosmetically undesirable), skin conditions, due to chronoageing or photoageing, such as wrinkles, lines, sagging, hyperpigmentation and age spots, may be obtained through the application of cosmetic compositions to the skin which comprise a specific fatty acid—petroselinic acid and/or derivatives thereof, in combination with a retinoid and/or an inhibitor of the enzyme acyl CoA retinol transferase (ARAT) or the enzyme lecithin retinol acyl transferase (LRAT) (hereinafter referred to as LRAT/ARAT inhibitors). We have also found that the use of such cosmetic compositions advantageously provides further skin care benefits in addition to anti-ageing such as soothing sensitive and/or irritated skin, controlling oil/sebum secretion and for lightening the skin.

The art discussed above does not disclose the specific synergistic combination of petroselinic acid with retinoids/LRAT/ARAT inhibitors nor the use of such a specific combination for treating wrinkles sensitive skin, dry skin, controlling oil/sebum secretion, or lightening skin.

SUMMARY OF THE INVENTION

According to a first aspect of the present invention there is provided a topical composition comprising:

(a) petroselinic acid and/or derivatives thereof;
(b) a retinoid and/or an LRAT/ARAT inhibitor; and
(c) a dermatologically acceptable vehicle.

According to a second aspect of the present invention there is provided a cosmetic method of providing at least one skin care benefit selected from: treating/preventing wrinkling, sagging, dry, aged and/or photodamaged skin; boosting collagen deposition in skin, boosting decorin production in skin, enhancing tissue repair; soothing irritated, red and/or sensitive skin; improving skin texture, smoothness and/or firmness; lightening skin; controlling oil/sebum secretion, the method comprising applying to the skin a topical composition as described above.

The present invention also encompasses the use of the inventive compositions for providing at least one skin care benefit selected from treating/preventing wrinkling, sagging, aged and/or photodamaged skin; boosting collagen deposition in skin, boosting decorin production in skin, enhancing tissue repair; soothing irritated, red and/or sensitive skin; improving skin texture, smoothness and/or firmness; lightening skin; controlling oil/sebum secretion.

According to a still further aspect of the present invention there is provided the use of petroselinic acid and derivatives thereof in combination with a retinoid and/or a LRAT/ARAT inhibitor in a cosmetic topical composition for providing at least one cosmetic skin care benefit selected from treating/preventing wrinkling, sagging, aged and/or photodamaged skin; boosting collagen deposition in skin, boosting decorin production in skin, enhancing tissue repair; soothing irritated, red and/or sensitive skin; improving skin texture, smoothness and/or firmness; lightening skin; and controlling oil/sebum secretion.

The inventive compositions, methods and uses thus provide anti-aging benefits which result in the promotion of smooth and supple skin with improved elasticity and a reduced or delayed appearance of wrinkles and aged skin, with improved skin colour. A general improvement in the appearance, texture and condition, in particular with respect to the radiance, clarity, and general youthful appearance of skin is achieved. The inventive compositions, methods and uses are also beneficial for soothing and calming sensitive and/or irritated skin, for lightening skin and for controlling oil/sebum secretion. Thus the present invention advantageously provides a wide range of skin care benefits.

The term "treating" as used herein includes within its scope reducing, delaying and/or preventing the above mentioned normal skin conditions such as wrinkled, aged, and/or photodamaged, and/or irritated skin and generally enhancing the quality of skin and improving its appearance and texture by preventing or reducing irritation, wrinkling and increasing flexibility, firmness, smoothness, suppleness and elasticity of the skin, all for cosmetic purposes. The compositions, methods and uses according to the invention may be useful for treating skin which is already in a wrinkled, aged, photodamaged, irritated condition or for treating youthful skin to prevent or reduce those aforementioned undesirable changes due to the normal ageing/photoageing process.

DETAILED DESCRIPTION OF THE INVENTION

Petroselinic Acid

Petroselinic acid (hereinafter referred to as PA) is a monounsaturated long chain (C18) fatty acid, having the formula $CH_3(CH_2)_{10}CH=CH(CH_2)_4COOH$.

The invention also includes derivatives of the free acid which thus comprise petroselinic acid moieties. Preferable derivatives include those derived from substitution of the carboxyl group of the acid, such as esters (eg triglyceride esters, monoglyceride esters, diglyceride esters, phosphoesters), amides (eg ceramide derivatives), salts (eg alkali metal and alkali earth metal salts, ammonium salts); and/or those derived from substitution of the C18 carbon chain, such as alpha hydroxy and/or beta hydroxy derivatives.

In the case of triglyceride ester derivatives, all positional isomers of PA substituents on the glycerol backbone are included. The triglycerides must contain at least one PA moiety. For example, of the three esterifiable positions on the glycerol backbone, the 1 and 2 positions may be esterified with PA and by another lipid at position 3 or as an alternative, the glycerol backbone could be esterified by PA at the 1 and 3 positions with another lipid at position 2.

Oils that are rich in petroselinic acid triglyceride are thus also suitable for use in the present invention. Such oils are commercially available and include parsley seed oil, carrot seed oil, fennel fruit oil, parsnip seed oil, coriander seed oil, chervil seed oil, caraway plant oil, and celery seed oil.

Wherever the term "petroselinic acid" or "PA" is used in this specification it is to be understood that the derivatives thereof comprising PA moieties are also included. "PA moieties" refers to PA fatty acyl portion(s) of a PA derivative.

The PA to be employed in accordance with the present invention is present in the topical composition in an effective amount. Normally the total amount of the active is present in an amount between 0.0001% and 50% by weight of the composition. More preferably the amount is from 0.01% to 10% and most preferably from 0.1% to 5% in order to maximize benefits at a minimum cost.

Retinoid

The term "retinoid" inter alia includes retinoic acid, retinoyl ester, retinol, retinyl ester.

The term "retinol" includes the following isomers of retinol: all-trans-retinol, 13-cis-retinol, 11-cis-retinol, 9-cis-retinol, 3,4-didehydro-retinol. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. The term "retinol" has been defined above. Retinyl esters suitable for use in the present invention are $C_1$–$C_{30}$ esters of retinol, preferably $C_2$–$C_{20}$ esters, and most preferably $C_2$–$C_3$, and $C_{16}$ esters because they are more commonly available. The preferred esters for use in the present invention are selected from, retinyl palmitate, retinyl acetate, retinyl propionate and retinyl linoleate, because these are the most commercially available and therefore the cheapest. Retinyl ester is also preferred due to its efficacy.

Retinoyl ester is an ester of retinoic acid. Retinoyl esters suitable for use in the present invention include $C_1$–$C_{30}$ esters of retinoic acid, preferably $C_2$–$C_{20}$ esters and most preferably $C_2$–$C_3$ and $C_{16}$ esters. The preferred esters for use in the present invention are selected from retinoyl linoleate, retinoyl palmitate, retinoyl oleate, retinoyl ascorbate, and retinoyl linolenate.

LRAT/ARAT Inhibitor

Retinol is an endogenous compound that occurs naturally in the human body and is essential for normal epithelial cell differentiation. Esters of retinol hydrolyze in-vivo to produce retinol. It is believed that retinyl esters and retinol are metabolically converted in the skin into retinoic acid according to the following mechanism

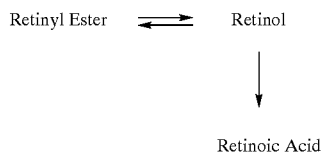

However, most of the endogenously applied retinol is rapidly converted into inactive fatty esters for storage in epidermal cells (keratinocytes).

Esterification of retinol into inactive retinyl esters is achieved in cells by transfer of a fatty acyl group from an acyl CoA, catalyzed by the enzyme acyl CoA retinol transferase (ARAT), or by the transfer of an acyl group from phosphatidyl choline, catalyzed by the enzyme lecithin retinol acyl transferase (LRAT). These esterification reactions are very efficient in keratinocytes—the majority (95%) of cellular retinoids are in the form of retinyl fatty esters.

The term "LRAT/ARAT inhibitor" in the present application thus means an agent which inhibits these esterification reactions and thus potentiates the action of retinol by increasing the amount of retinol available for conversion to retinoic acid.

The LRAT/ARAT inhibitors within the scope of the present invention are identifiable as those compounds which at 100 μM concentration inhibit at least 20% of LRAT or ARAT catalyzed retinol esterification as measured by the in vitro Microsomal Assay described below in Example 1. In a preferred embodiment of the invention, the LRAT/ARAT inhibitor is a compound that at 100 μM concentration inhibits at least 40% and most preferably at least 50% of LRAT or ARAT catalysed retinol esterification. The in vitro Microsomal Assay employed for determining whether or not a compound is such a LRAT/ARAT inhibitor is as described in Example 1 below.

Thus if a compound passes this in vitro Microsomal assay, that is, it inhibits sufficiently an LRAT or ARAT catalysed retinol esterification as measured by the in vitro Microsomal Assay, it is included in the present invention even if it is not specifically mentioned herein.

Examples of such LRAT/ARAT inhibitors which satisfy the assay described in Example 1 include fatty acid amides, hydroxy fatty acid amides, ceramides, melinamide, imidazolidinones, and cyclic aliphatic unsaturated hydrocarbons, terpenes, and fatty hydroxyethyl imidazoline surfactants.

Cyclic Aliphatic Unsaturated Compounds

Suitable cyclic aliphatic unsaturated compounds are selected according to the in-vitro Microsomal Assay Test described above.

A preferred cyclic aliphatic unsaturated compound is selected from cyclic aliphatic unsaturated aldehydes, ketones, alcohols and esters such as alpha damascone, beta damascone, delta damascone, isodamascone, damascenone, alpha ionone, beta ionone, allyl alpha ionone, isobutyl ionone, alpha methyl ionone, gamma methyl ionone, brahmanol, sandanol, alpha terpineol, lyral, ethyl saffranate, and mixtures thereof. Preferably, in order to maximize performance at a minimum cost, a cyclic aliphatic unsaturated compound is selected from the group consisting of damascones and ionones.

Most preferably, the cyclic aliphatic unsaturated compound is a α-Damascone and/or α-Ionone.

Diterpenes

Suitable diterpenes are selected according to the in-vitro Microsomal Assay Test described above. A preferred diterpene compound is geranyl geraniol, which is a potent inhibitor of retinol esterification.

Fatty Hydroxethyl Imidazoline Surfactants

Fatty hydroxyethyl imidazoline surfactants included in the present invention pass the in-vitro Microsomal Assay test described above. Preferred fatty hydroxyethyl imidazolines have the following general structure:

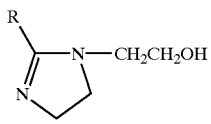

wherein R is an aliphatic saturated or unsaturated, straight or branched hydro-carbon chain containing from 8 to 20 carbon atoms.

Preferably, R in the fatty hydroxyethyl imidazoline contains from 8 to 18 carbon atoms, more preferably from 11 to 18 carbon atoms. Most preferably, the fatty hydroxyethyl imidazoline is oleyl hydroxyethyl imidazoline, due to its commercial availability and efficacy.

Fatty Acid Amide

Preferably, the fatty acid amide contains at least 6 carbon atoms. Suitable fatty acids include saturated and unsaturated, straight or branched fatty acids. Suitable fatty acids preferably contain from 8 to 24 carbon atoms, preferably from 12 to 20 carbon atoms, and most preferably from 12 to 18 carbon atoms, because longer chain fatty acid amides are more beneficial for conditioning of the skin. In the most preferred embodiment of the invention, amides of essential fatty acids are employed because essential fatty acids provide nutrition for the skin. Examples of essential fatty acids include but are not limited to linoleic, linolenic, arachidonic, gamma-linolenic, homo-gamma-linolenic, and mixtures thereof. Linoleic acid is most preferred because it is also a precursor to ceramide.

The preferred amides included in the present invention are mono- and di-alkanol amides, particularly of essential fatty acids. Alkanol amides are more commonly available than alkyl amides.

The most preferred fatty acid amides are selected from mono- and diethanolamides and phosphatidylethanolamides of linoleic acid, palmitic acid, and coconut oil; diethyl cocamide, linoleamidyl dimethylamine, dimethyl linoleamide, diethyl linoleamide, dimethyl palmitide, myristoyl sarcosine.

Hydroxy Fatty Acid Amides

The structure of an amide of a hydroxy fatty acid is as follows:

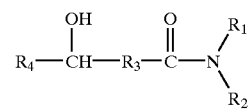

wherein $R_1$, $R_2$ and $R_4$ each is independently selected from hydrogen and aliphatic saturated or unsaturated, straight or branched hydrocarbon chains which may be hydroxylated, containing from 1 to 20 carbon atoms;

$R_3$ is $-(CH_2)_n$ where n is an integer from 0 to 18;

Preferably, $R_1$, $R_2$, $R_4$ each independently contains from 2 to 20 carbon atoms, more preferably from 2 to 15 carbon atoms, most preferably from 3 to 13 carbon atoms.

Preferably the hydroxy acid amide is an amide of α- or β-hydroxy acid, i.e., n is 0 or 1.

The most preferred hydroxy fatty acid amides to be included in the inventive compositions are: lactamide-monoethanolamide, $C_{13}$-β-hydroxy acid amide (2-hydroxy-$C_{13}$-amide), N-hydroxyethyl-2-hydroxy-$C_{16}$ amide, 12-hydroxy-N-(2-hydroxyethyl) octadecanamide, and monoethanolamide of castor oil.

Polycyclic Triterpene Carboxylic Acid (PTCA)

A further example of a suitable LRAT/ARAT inhibitor is a PCTA which passes the in vitro Microsomal Assay.

Preferably the PTCA is a pentacyclic triterpene monocarboxylic acid.

Most preferably, PTCA is selected from the group consisting of ursolic acid, oleanolic acid, glycerrhetinic and glycyrrhizic acid.

PTCA are commercially available from Aldrich and Sigma. Plant extracts containing PTCA are suitable for use in the present invention e.g. *Rosmarinus officinalis* (rosemary), Diospyros spp. (persimmon), *Forsythia suspensa* (forsythia), *Lavandula angustifolia* (lavender), *Prunella vulgaris* (selfheal), *Paeonia lactifolia, Glycyrrhiza glabra* (licorice).

It should be understood that depending on the pH of the composition, PTCA may be present in the composition as a salt, e.g. alkali or alkaline earth salt.

Ceramides

The ceramides may for example be naturally occurring ceramides, phyto ceramides, short chain ceramides, pseudoceramides or neoceramides. The general structure of these molecules is described in U.S. Pat. No. 5,476,661 (Pillai et al.) whose contents are hereby incorporated by reference.

The most preferred ceramide derivative is acetyl sphingosine due to its efficacy.

The retinoid and/or LRAT/ARAT inhibitor can be included in the inventive compositions in an amount ranging from 0.0001% to 50% by weight of the composition, preferably it is used in an amount of from 0.01% to 10%, most preferably from 0.1% to 5%.

Dermatologically Acceptable Vehicle

The composition used according to the invention also comprises a dermatologically/cosmetically acceptable vehicle to act as a diluant, dispersant or carrier for the actives.

The vehicle may comprise materials commonly employed in skin care products such as water, liquid or solid emollients, silicone oils, emulsifiers, solvents, humectants, thickeners, powders, propellants and the like.

The vehicle will usually form from 5% to 99.9%, preferably from 25% to 80% by weight of the composition, and can, in the absence of other cosmetic adjuncts, form the balance of the composition.

Optional Skin Benefit Materials and Cosmetic Adjuncts

Besides the actives, other specific skin-benefit actives such as sunscreens, other skin lightening agents, skin tanning agents may also be included. The vehicle may also further include adjuncts such as perfumes, opacifiers, preservatives, colourants and buffers.

Product Preparation, Form, Use and Packaging

To prepare the topical composition used in the method of the present invention, the usual manner for preparing skin care products may be employed. The active components are generally incorporated in a dermatologically/cosmetically acceptable carrier in conventional manner. The active components can suitably first be dissolved or dispersed in a portion of the water or another solvent or liquid to be incorporated in the composition. The preferred compositions are oil-in-water or water-in-oil or water-in-oil-in-water emulsions.

The composition may be in the form of conventional skin-care products such as a cream, gel or lotion, capsules or the like. The composition can also be in the form of a so-called "wash-off" product e.g. a bath or shower gel, possibly containing a delivery system for the actives to promote adherence to the skin during rinsing. Most preferably the product is a "leave-on" product, i.e. a product to be applied to the skin without a deliberate rinsing step soon after its application to the skin.

The composition may packaged in any suitable manner such as in a jar, a bottle, tube, roll-ball, or the like, in the conventional manner. It is also envisaged that the inventive compositions could be packaged as a kit of two separate compositions one containing the petroselinic acid and the second containing the retinoid/LRAT/ARAT inhibitor compound, to be applied to the skin simultaneously or consecutively.

The composition according to the present invention may also be formulated in a form suitable for oral ingestion such as a capsule, tablet or the like.

The method of the present invention may be carried out one or more times daily to the skin which requires treatment. The improvement in skin appearance will usually become visible after 3 to 6 months, depending on skin condition, the concentration of the active components used in the inventive method, the amount of composition used and the frequency with which it is applied. In general, a small quantity of the topical composition, for example from 0.1 to 5 ml is applied to the skin from a suitable container or applicator and spread over and/or rubbed into the skin using the hands or fingers or a suitable device. A rinsing step may optionally follow depending on whether the composition is formulated as a "leave-on" or a "rinse-off" product.

In order that the present invention may be more readily understood, the following examples are given, by way of illustration only.

EXAMPLES

Example 1

This example demonstrates how LRAT/ARAT inhibitors within the scope of the present invention may be identified using the in vitro Microsomal Assay of the esterification of retinol.

Method of In vitro Microsomal Esterification of Retinol

Microsomes are obtained as described in: J. C. Saari and D. L. Bredberg, "CoA and Non-CoA Dependent Retinol Esterification in Retinal Pigment Epithelium" J. Biol. Chem. 23, 8084–90 (1988).

A solution containing 0.1 M sodium phosphate pH 7 buffer, 5 mM dithiothreitol, 2 mg/ml bovine serum albumin, 40 micromolar palmitoyl CoA, 40 micromolar dilauroyl phosphatidyl choline, 10 micromolar retinol and a test compound or solvent blank, was incubated for 1 hour at 37° C. with a microsomal fraction isolated from bovine retinal pigment epithelial cells. After incubation, the reaction was quenched by addition of an equal volume of ethanol, and the retinyl esters formed (retinyl palmitate from the ARAT catalyzed reaction, and retinyl laurate from the LRAT catalyzed reaction) were extracted with hexane. The hexane layer was removed, evaporated under nitrogen, and the residue analyzed by HPLC on a 3.9×300 mm C18 reversed phase column using a 80% methanol in tetrahydrofuran mobile phase and fluorescence detection (325 nm excitation, 480 nm emission) to quantitate the retinyl esters. The quantity of ester formed in the presence of the solvent blank was taken as 100%, and this was used to calculate the percent inhibition of ester formation for the compounds tested. As a control, an aliquot of microsomes was inactivated by boiling for 5 minutes, which resulted in at least 95% inhibition of ester formation.

The results that were obtained are summarized in Table 1.

TABLE 1

| COMPOUND | CONCENTRATION ($\mu$M) | % INHIB. ARAT | % INHIB. LRAT |
| --- | --- | --- | --- |
| Acetyl Sphingosine | 100 | 62 | 50 |
| Acetyl Sphingosine | 10 | 19 | 10 |
| Linoleamide-DEA (LODEA) | 100 | 43 | 51 |
| Linoleamide-DEA | 10 | 12 | 11 |
| Linoleamide-MEA (LOMEA) | 100 | 35 | 35 |
| Linoleamide-MEA | 10 | 0 | 0 |
| oleyl hydroxyethyl imidazoline | 100 | 90 | 95 |
| oleyl hydroxyethyl imidazoline | 10 | 14 | 28 |
| caprylic hydroxyethyl imidazoline | 100 | — | 8 |
| diazolidinyl urea | 100 | 0 | 0 |
| thiamine | 100 | 0 | 0 |
| caffeine | 100 | 0 | 0 |
| adenine | 100 | 0 | 0 |
| phenyl benzimidazole sulfonic acid | 100 | 0 | 0 |
| uracil | 100 | 0 | 0 |
| tryptophan | 100 | 0 | 0 |

It can be seen that acetyl sphingosine, LODEA, LOMEA and hydroxyethyl imidazoline surfactant are a potent retinol esterification inhibitors, while other surfactants and other heterocyclic compounds were essentially inactive. Caprylic hydroxyethyl imidazoline (R=$CH_3(CH_2)_6$) did not sufficiently inhibit LRAT.

The in vitro Microsomal Assay Test was run on the compounds listed in Tables 2A and 2B.

The compounds in Table 2A were tested at a 100 $\mu$M concentration. The compounds in Table 2B were tested at a 10 $\mu$M concentration.

TABLE 2A

| COMPOUND | % INHIBITION, ARAT | % INHIBITION, LRAT |
| --- | --- | --- |
| Alpha damascone | 83 | 98 |
| Beta damascone | 84 | 92 |
| Delta damascone | 87 | 95 |
| Isodamascone | 80 | 92 |
| Damascenone | 70 | 79 |
| Alpha ionone | 45 | 49 |
| Beta ionone | 22 | 24 |
| Allyl alpha ionone | 22 | 36 |
| Isobutyl ionone | 8 | 45 |
| Alpha methyl ionone | 67 | 77 |
| Gamma methyl ionone | 21 | 38 |
| Brahmanol | 70 | 75 |
| Sandanol | 15 | 43 |
| Alpha terpineol | 26 | 25 |
| Timberol | 34 | 33 |
| Lyral | 76 | 71 |
| Tonalid | 50 | 33 |
| Ethyl saffranate | 51 | 49 |
| Traseolide | 41 | 21 |
| Sandalone | 23 | 12 |

TABLE 2B

| COMPOUND | % INHIBITION, ARAT | % INHIBITION, LRAT |
| --- | --- | --- |
| alpha damascone | 67 | 87 |
| beta damascone | 45 | 52 |
| delta damascone | 58 | 64 |
| damascenone | 23 | 29 |
| allyl alpha ionone | 16 | 17 |

It can be seen from the results in Tables 2A and 2B that certain cyclic aliphatic unsaturated compounds in particular the ionones and damascones are potent inhibitors of LRAT and ARAT catalyzed retinol esterification. These contain the trimethyl cyclohexene ring system present in retinol.

The in-vitro Microsomal Assay test was conducted with additional cyclic aliphatic unsaturated compounds. The results that were obtained are summarized in Table 3.

The compounds in Table 3 were tested at a 100 $\mu$M concentration.

TABLE 3

| COMPOUND | % INHIBITION, ARAT | % INHIBITION, LRAT |
| --- | --- | --- |
| dihydro alpha ionone | 13 | 18 |
| alpha ionol | 0 | 0 |
| beta ionol | 0 | 0 |
| cinnamaldehyde | 0 | 0 |
| vanillin | 0 | 0 |
| eucalyptol | 0 | 0 |
| menthol | 0 | 0 |
| thymol | 0 | 0 |
| carvone | 0 | 0 |
| camphor | 0 | 0 |
| mentone | 0 | 0 |
| fenchyl alcohol | 12 | 4 |
| isocyclogeraniol | 18 | 16 |
| dimethyl ionone | 0 | 9 |
| delta methyl ionone | 0 | 10 |

It can be seen from the results in Table 3 that not all cyclic aliphatic unsaturated compounds inhibit or sufficiently inhibit LRAT and ARAT catalyzed retinol esterification.

The in-vitro Microsomal Assay test was conducted with a diterpene compound, geranyl geraniol or farnesol.

The results that were obtained are summarized in Table 4.

TABLE 4

| COMPOUND | CONCENTRATION ($\mu$M) | % INHIB. ARAT | % INHIB. LRAT |
| --- | --- | --- | --- |
| Geranyl Geraniol[1] | 100 | 81 | 77 |
| Geranyl Geraniol | 10 | 38 | 16 |
| Farnesol[2] | 100 | 43 | 43 |
| Farnesol | 10 | 20 | 10 |

[1]Obtained from TCI America (Portland,Oregon). Also available from Sigma and CTC Organics (Atlanta, Georgia).
[2]Available from Givaudan Co., Bedoukian Co., or Dragoco Co.

It can be seen from the results in Table 4 that both geranyl geraniol and farnesol inhibit retinol esterification. Geranyl geraniol is a substantially more potent esterification inhibitor, than farnesol.

Example 2
Identification of Procollagen-I and Decorin Upregulation in Skin In Vivo Following Topical Retinoic Acid Treatment for Comparative Purposes Collagen, the predominant matrix skin protein is known to impart tensile strength to skin. Decorin is a proteoglycan which is known to be important for controlled and correct deposition of collagen in the extracellular matrix of skin. It is also known in the art that the levels of collagen and decorin in skin are significantly reduced with aged and/or photodamaged skin. Many studies have shown that the levels of collagen type I in skin is decreased with age and/or with increased photodamage, (for example Lavker, R. J.Inv.Derm.,(1979),73,79–66; Griffiths et al. N. Eng. J. med. (1993) 329, 530–535). In the case of decorin, it has been shown that mRNA expression and expression of the proteoglycan is greatly reduced in photodamaged skin in vitro (Bernstein et al. Lab. Invest. (1995)72,662–669). The reduction of the levels of these skin proteins is accordingly associated with a decrease in the tensile strength of the skin causing wrinkles and laxity.

It is well known in the art that retinoic acid is a potent anti-aging active and induces dermal repair of photodamaged skin. It has been shown that wrinkle effacement and dermal repair following topical treatment of skin with retinoic acid arises through new collagen deposition and synthesis in the skin (for example, Griffiths et al. N. Eng. J. med. (1993) 329, 530–535). It is widely accepted that strengthening of the dermal matrix by boosting the level of collagen in skin using retinoic acid provides anti-ageing/dermal repair benefits. Procollagen I is a precursor of collagen. Increased production of procollagen I in response to a test compound application is a marker of an increased collagen level.

Two groups of women were recruited with identical or nearly identical degrees of mild to moderate photodamage on each outer forearm. They were supplied with 0.05% retinoic acid in a moisturising base (Retinova®) and also with a colour matched moisturising cream with similar sensory characteristics (Dermacare® lotion), but no active ingredients, as a placebo control. Each participant of the two groups applied the Retinova® to one outer forearm and placebo (Dermacare®) to the other outer forearm. Group 1 applied the products daily to their outer forearms for 14 weeks and the Group 2 applied the products to their outer forearms for 28 weeks. At the end of the studies two full thickness 4 mm punch biopsies were taken from the treated areas of each forearm. Immunohistochemical analysis of the biopsy tissue taken from the participants was performed to identify the effect of retinoic acid treatment on the expression of the skin extracellular matrix components, decorin and procollagen-I, as compared with the placebo treated forearms. The following procedure was followed:

Materials

Antibody dilution buffer for wax sections was composed of Tris Buffered Saline (TBS), 3% bovine serum albumin (BSA), 0.05% Triton X-100 and 0.05% sodium azide. Primary antibodies for procollagen-I (amino terminal) were obtained from Chemicon International Inc. (cat# MAB 1912, rat IgGl) and used on wax sections at a dilution of 1:800, overnight at 4° C. after the section had been pretreated with trypsin (0.5 mg/ml, 25 minutes, 37° C.). Primary antibodies for decorin were obtained from Biogenesis (rabbit polyclonal) and used on wax sections at a dilution of 1:800, overnight at 4° C. Anti-rat biotinylated secondary antibodies, obtained from DAKO (cat# E0468, rabbit polyclonal), were applied to wax sections at a dilution of 1:400. Anti-rabbit biotinylated secondary antibodies, obtained from Amersham (cat# RPN 1004, donkey polyclonal), were applied to wax sections at a dilution of 1:400. Streptavidin conjugated alkaline phosphatase, obtained from Zymed (cat# 43-4322), was used at a concentration of 1:2500. Fast Red chromogen was obtained from DAKO (cat# K597). Gills #3 Haemotoxylin nuclear counterstain obtained from Sigma (cat# GHS-3), was filtered and used without dilution. Trypsin was obtained from Sigma (cat# T-7186) and slides were mounted with Glycergel from DAKO (cat# C563).

Methods

Wax sections of the biopsy tissue were mounted on silane coated slides and baked for 18 hours at 55° C. The slides were de-waxed through xylene and alcohol and brought to water and then transferred to TBS. DAKO® pen was used to ring the sections. The sections were processed for antigen retrieval using trypsin where necessary, as indicated for each antibody. Where antigen retrieval was necessary, the slides were incubated for 25 minutes at 35° C. with trypsin at 0.5 mg/ml (Sigma Cat # T-7186). The protease was subsequently rinsed off (2x2 minutes) with TBS. Following antigen retrieval, if necessary, or otherwise directly after ringing the sections, non specific antibody binding was blocked with 5% solutions of secondary antibody host serum in TBS/0.5% BSA/0.1% sodium azide as the blocking solution for at least 20 minutes at room temperature in a humid chamber. The excess blocking solution was drained off, but the sections were not allowed to dry. The sections were then incubated with the primary antibody (appropriately diluted as indicated above) in a humid chamber overnight at 4° C. Antibody was subsequently drained from the sections, without allowing them to dry. The slides were then washed with TBS to remove unbound primary antibody—a one minute rinse followed by three five minute washes—and then incubated with the appropriate secondary antibody (appropriately diluted as indicated above) in a humid chamber for 1 hour at room temperature.

The antibody solution was subsequently drained from the slides without allowing the section to dry. The slides were washed in TBS, a one minute rinse followed by 4x5 min washes, in order to remove the unbound secondary antibody. For the biotinylated secondary antibody the sections were subsequently incubated with streptavidin conjugate for 45 minutes at 37° C. and then washed in TBS to remove unbound streptavidin conjugate. The chromogen was added and the colour developed with observation to avoid overstaining. The sections were then counterstained and mounted.

Differences in the expression of procollagen-I and decorin between retinoic acid (Retinova®) and placebo (Dermacare®) treated sites were determined by visual assessment of the immunohistochemically stained sections using light microscopy.

This analysis identified marked upregulation of both procollagen-I and decorin in the photodamaged skin following topical application of retinoic acid (Retinova®), as set out in Table 5 below.

TABLE 5

Effect of Retinoic Acid Treatment on expression of procollagen I and decorin in skin In Vivo

| | Total No. of Participants | No. of Participants showing marked increase in expression of procollagen-I | No. of Participants showing marked increase in expression of decorin |
|---|---|---|---|
| Group 1 after 14 weeks | 16 | 9 | 10 |
| Group 2 after 28 weeks | 15 | 10 | 15 |

The extra cellular matrix components procollagen 1 and decorin are thus clearly identifiable markers of retinoic acid induced dermal repair.

Example 3

Procedure for Measuring Procollagen-I and Decorin Synthesis in Human Dermal Fibroblasts Preparation of Dermal Fibroblast Conditioned Medium Primary human foreskin fibroblasts at passage 2 (P2) were seeded into 12-well plates at 10000 cells/cm$^2$ and maintained for 24 hours in an atmosphere of 5% carbon dioxide and 4% oxygen in Dulbeccos Modified Eagles Medium (DMEM) supplemented with 10% foetal calf serum. After this time the cells were washed with serum free DMEM and then incubated in fresh serum free DMEM for a further 60 hours. The fibroblast monolayers were then washed again with serum free DMEM. Test reagents and vehicle controls were added to the cells in triplicate in a final volume of 0.4 ml/well fresh serum free DMEM and incubated for a further 24 hours. This fibroblast conditioned medium was either analysed immediately or snap frozen in liquid nitrogen and stored at −70° C. for future analysis. The cells were then counted and data from the dot-blot analysis subsequently standardised to cell number.

Example 4

Dot Blot Assay for Procollagen-I and Decorin Protein in Dermal Fibroblast Conditioned Medium Samples of conditioned medium from dermal fibroblasts treated with vehicle (as a control) or test reagents were supplemented with 20 mM dithiothreitol (1:10 dilution of 200 mM stock solution) and 0.1% sodium dodecylsulphate (1:100 dilution of 10% stock solution), mixed well and then incubated at 75° C. for 2 minutes. A standard for the assay was generated by serial dilution of neat fibroblast conditioned medium from fibroblasts seeded at 10000 cells/cm$^2$ in a 175 cm$^2$ flask and maintained in serum free DMEM as described above.

Assay samples were subsequently applied in triplicate to a prewetted sheet of Immobilon-P transfer membrane using the 96-well Bio-Dot Apparatus from Bio-Rad as described in the manufacturers guidelines. Approximately 200 µl of medium was applied per well. The medium was allowed to filter through the membrane under gravity (30 minutes) after which the membrane was washed twice with PBS (200 µl).

These PBS washes were allowed to filter through the membrane under gravity (2×15 minutes). The Bio-Dot apparatus was then attached to a vacuum manifold and a third and final PBS wash carried out under suction. The apparatus was disassembled, the membrane removed and quickly cut as required before being placed in blocking buffer overnight at 4° C. Membranes prepared for decorin analysis were blocked with 3% (w/v) BSA/0.1% (v/v) Tween 20 in PBS, whilst those for procollagen-I analysis were blocked with 5% (w/v) non fat dried milk powder/0.05% Tween 20 in PBS.

The following day, the membranes were probed with 1:10000 dilution of primary antibodies to either human procollagen-I (MAB1912; rat monoclonal; Chemicon Int. Inc., Temecula, Calif.) or human decorin (rabbit polyclonal; Biogenesis) for 2 hours at room temperature. The membranes were subsequently washed with TBS/0.05% Tween 20 (3×5 minutes) and then incubated with 1:1000 dilution of $^{125}$I-conjugated anti-rat or anti-rabbit F(ab')2 fragments (Amersham) as required for 1 hour at room temperature. Following this the Immobilon strips were again washed with TBS/Tween 20 (3×5 minutes) before being allowed to dry in air at room temperature. The dried membranes were wrapped in cellophane and exposed to a Molecular Dynamics storage phosphor screen for 16–18 hours. At the end of this time the exposed screen was scanned by a phosphorimager (Molecular Dynamics Phosphorimager SF) using ImageQuant™ software. Dot intensity was assessed by computer-assisted image analysis using the quantification tools in ImageQuant™, standardised to cell number and the effects of various test reagents on decorin and procollagen-I synthesis were determined relative to a vehicle treated control value of 100 arbitrary units.

Example 5

Tests

The table below indicates the synergistic effect of petroselinic acid in combination with the LRAT/ARAT inhibitors Ceramide 6 or LOMEA on procollagen-I and decorin synthesis in human dermal fibroblasts, and the amounts in which the actives were applied. In order to normalise the results the effects of the test substances were determined relative to a vehicle treated control value of 100 arbitrary units. The concentrations of reagents used in the trials had no influence on cell viability.

TABLE 6

The Synergistic Effect on Procollagen-I and/or Decorin Synthesis by Petroselinic Acid in combination with a LRAT/ARAT Inhibitor

| Treatment | Procollagen-I | Decorin |
| --- | --- | --- |
| Control (Vehicle) | 100 | 100 |
| 0.01 μM PA | 85.1% | |
| 0.01 μM Ceramide 6 | 94.3% | |
| 0.01 μM PA + 0.01 μM Ceramide 6 | 125.6% | |
| 0.01 μM PA | | 101.8% |
| 0.1 μg/ml LOMEA | | 133.9% |
| 0.1 μM PA + 0.1 μg/ml LOMEA | | 239.1% |

The results in table 6 indicate that the combination of petroselinic acid with a LRAT/ARAT inhibitor significantly upregulates the synthesis of procollagen-I and/or decorin in human dermal fibroblasts as compared to the control.

The level of decorin in skin is associated with improved condition and appearance of skin. Increasing the level of decorin in skin is important for controlled and correct deposition of collagen in skin which is associated with many skin benefits such as wrinkle effacement and dermal repair of photodamaged skin.

Synergy of Petroselinic Acid with Retinoids

The table below indicates the synergistic effect of petroselinic acid in combination with the retinoids on procollagen-I and/or decorin synthesis in human dermal fibroblasts, and the amounts in which the actives were applied. In order to normalise the results the effects of the test substances were determined relative to a vehicle treated control value of 100 arbitrary units. The concentrations of reagents used in the trials had no influence on cell viability.

TABLE 7

Untreated control = 100%. All results normalised to this value.

| Actives Tested | Procollagen 1 | Decorin |
| --- | --- | --- |
| 0.01 μM PA | | 100.5% |
| 0.01 μM trans Retinoic acid | | 102.8% |
| 0.01 μM PA + 0.01 μM trans Retinoic acid | | 133.4% |
| 0.01 μM PA | 86.0% | |
| 0.01 μM Retinol | 95.0% | |
| 0.01 μM PA + 0.01 μM Retinol | 126.4% | |
| 0.01 μM PA | | 107.5% |
| 0.1 μM Retinyl Linoleate | | 109.1% |
| 0.01 μM PA + 0.1 μM Retinyl Linoleate | | 122.3% |

The results in table 7 indicate that the combination of petroselinic acid with a retinoid significantly upregulates the synthesis of procollagen-I and/or decorin in human dermal fibroblasts as compared to the control.

The level of decorin in skin is associated with improved condition and appearance of skin. Increasing the level of decorin in skin is important for controlled and correct deposition of collagen in skin which is associated with many skin benefits such as wrinkle effacement and dermal repair of photodamaged skin.

Example 6

This example illustrates oil-in-water creams according to the invention.

| | % w/w | | | | |
| --- | --- | --- | --- | --- | --- |
| | A | B | C | D | E |
| Petroselenic acid (triglyceride) ex NU Check Prep | 1.15 | 1.15 | 3 | 2 | 1 |
| Retinyl Linoleate | | | | | 0.15 |
| Retinoic acid | — | | 0.001 | — | |
| Retinol | 0.15 | — | | 0.15 | |
| Mineral oil | 4 | 4 | 4 | 4 | 4 |
| α-ionone | 1 | — | — | — | — |
| Isodamascone | — | — | 0.3 | — | — |
| Brij 56* | 4 | 4 | 4 | 4 | 4 |
| Alfol 16RD* | 4 | 4 | 4 | 4 | 4 |
| Triethanolamine | 0.75 | 0.75 | 0.75 | 0.75 | 0.75 |
| Butane-1,3-diol | 3 | 3 | 3 | 3 | 3 |
| Xanthan gum | 0.3 | 0.3 | 0.3 | 0.3 | 0.3 |
| Perfume | qs | qs | qs | Qs | qs |
| Butylated hydroxy toluene | 0.01 | 0.01 | 0.01 | 0.01 | 0.01 |
| Water | to 100 | to 100 | to 100 | To 100 | to 100 |

*Brij 56 is cetyl alcohol POE (10) Alfol 16RD is cetyl alcohol

Example 7

This example illustrates alcoholic lotions according to the invention.

|  | % w/w | | | |
| --- | --- | --- | --- | --- |
|  | A | B | C | D |
| PA (triglyceride) ex NU Check Prep | 1 | 0.15 | 0.15 | 2 |
| α-Damascone | 0.1 | — | 0.1 | — |
| Geranyl Geraniol | — | 1 | — | 0.2 |
| Ethanol | 40 | 40 | 40 | 40 |
| Perfume | Qs | qs | Qs | qs |
| Butylated hydroxy toluene | 0.01 | 0.01 | 0.01 | 0.01 |
| Water | to 100 | to 100 | To 100 | to 100 |

Example 8

This example illustrates a suncare cream incorporating the composition of the invention:

|  | % w/w |
| --- | --- |
| Coriander seed oil ex Loders Croklaan (PA triglyceride about 60–75% of total fatty acids) | 4% |
| Retinyl Linoleate | 0.01 |
| Cocoylhydroxyethylimidazoline | 0.1 |
| Silicone oil 200 cts | 7.5 |
| Glycerylmonostearate | 3 |
| Cetosteryl alcohol | 1.6 |
| Polyoxyethylene-(20)-cetyl alcohol | 1.4 |
| Xanthan gum | 0.5 |
| Parsol 1789 | 1.5 |
| Octyl methoxycinnate (PARSOL MCX) | 7 |
| Perfume | Qs |
| Color | QS |
| Water | to 100 |

Example 9

This example illustrates a high internal phase water-in-oil emulsion incorporating the inventive composition.

|  | % w/w | | | |
| --- | --- | --- | --- | --- |
|  | A | B | C | D |
| Petroselinic acid (triglyceride) ex NU check Prep | 1 | 2 | 0.5 | 3 |
| Retinol | 0.5 | — | — | — |
| LODEA | — | 2 | — | — |
| LOMEA ex. Rhone Poulenc | — | 1 | — | — |
| Fully hydrogenated coconut oil | 3.9 | 3.9 | 3.9 | 3.9 |
| Brij 92* | 5 | 5 | 5 | 5 |
| Bentone 38 | 0.5 | 0.5 | 0.5 | 0.5 |
| MgSO$_4$7H$_2$O | 0.3 | 0.3 | 0.3 | 0.3 |
| Butylated hydroxy toluene | 0.01 | 0.01 | 0.01 | 0.01 |
| Perfume | Qs | Qs | Qs | Qs |
| Water | To 100 | To 100 | To 100 | To 100 |

*Brij 92 is polyoxyethylene (2) oleyl ether

Examples 6 to 9 illustrate topical compositions according to the present invention. The compositions can be processed in conventional manner. They are suitable for cosmetic use. In particular the compositions are suitable for application to wrinkled, rough, dry, flaky, aged and/or photo-damaged skin to improve the appearance and the feel thereof as well as for application to healthy skin to prevent or retard deterioration thereof.

What is claimed is:

1. A topical composition comprising:
   (a) a petroselinic acid compound;
   (b) a retinoid selected from the group consisting of retinoic acid, retinol and retinyl linoleate; and
   (c) a dermatologically acceptable vehicle.

2. A topical composition according to claim 1 wherein the retinoid is retinol.

3. A topical composition according to claim 1 wherein the retinoid is retinyl linoleate.

4. A topical composition according to claim 1 wherein the petroselinic acid compound is selected from the group consisting of petroselinic acid, salts of petroselinic acid, petroselinic acid amides, petroselinic acid esters and combinations thereof.

5. A topical composition according to claim 1 wherein the petroselinic acid compound is sourced as coriander seed oil.

6. A topical composition comprising:
   (a) a petroselinic acid compound;
   (b) a Ceramide 6; and
   (c) a dermatologically acceptable vehicle.

7. A topical composition according to claim 6 wherein the petroselinic acid compound is selected from the group consisting of petroselinic acid, salts of petroselinic acid, petroselinic acid amides, petroselinic acid esters and combinations thereof.

8. A topical composition according to claim 6 wherein the petroselinic acid compound is sourced from coriander seed oil.

9. A topical composition consisting essentially of:
   (a) a petroselinic acid compound;
   (b) a fatty acid amide of linoleic acid; and
   (c) a dermatologically acceptable vehicle.

10. A topical composition according to claim 9, wherein the fatty acid amide is linoleoyl monoethanolamide.

11. A topical composition according to claim 9 wherein the petroselinic acid compound is selected from the group consisting of petroselinic acid, salts of petroselinic acid, petroselinic acid amides, petroselinic acid esters and combinations thereof.

12. A topical composition according to claim 9 wherein the petroselinic acid compound is sourced as coriander seed oil.

13. A cosmetic topical composition consisting essentially of:
   (a) a petroselinic acid compound;
   (b) farnesol; and
   (c) a dermatologically acceptable vehicle.

14. A topical composition according to claim 13 wherein the petroselinic acid compound is selected from the group consisting of petroselinic acid, salts of petroselinic acid, petroselinic acid amides, petroselinic acid esters and combinations thereof.

15. A topical composition according to claim 13 wherein the petroselinic acid compound is sourced as coriander seed oil.

* * * * *